United States Patent
Stevenson et al.

(10) Patent No.: US 6,362,260 B1
(45) Date of Patent: Mar. 26, 2002

(54) PHENOL-FREE PHOSPHITE STABILIZERS

(75) Inventors: Donald R. Stevenson; Duong Nguyen, both of Dover, OH (US)

(73) Assignee: Dover Chemical Corporation, Dover, OH (US)

( * ) Notice: Subject to any disclaimer, the term of this patent is extended or adjusted under 35 U.S.C. 154(b) by 0 days.

(21) Appl. No.: 09/471,067

(22) Filed: Dec. 22, 1999

(51) Int. Cl.$^7$ ............................. C08K 5/49; C08K 5/51
(52) U.S. Cl. .................... 524/115; 524/128; 558/156
(58) Field of Search ................. 524/115, 128; 558/156

(56) References Cited

U.S. PATENT DOCUMENTS

| | | |
|---|---|---|
| 3,047,608 A | 7/1962 | Friedman et al. |
| 3,205,250 A | 9/1965 | Hechenbleikner |
| 3,281,381 A | 10/1966 | Hechenbleikner |
| 4,206,103 A | 6/1980 | Kromolicki et al. |
| 4,290,976 A | 9/1981 | Hechenbleikner et al. |
| 4,739,000 A | * 4/1988 | Burton ..................... 524/128 |

* cited by examiner

*Primary Examiner*—Margaret Medley
*Assistant Examiner*—Cephia D. Toomer
(74) *Attorney, Agent, or Firm*—Hudak & Shunk Co. L.P.A.; Daniel J. Hudak

(57) ABSTRACT

Liquid organic phosphites of low volatility, based on pentaerythritol, alkyl alcohols and alkyl phenols, which are essentially phenol-free are disclosed. These phosphites are excellent stabilizers for polymers, especially PVC resins. The phenol-free phosphite stabilizers are compatible with mixed metal stabilizers and give excellent color and processing stability.

25 Claims, No Drawings

PHENOL-FREE PHOSPHITE STABILIZERS

FIELD OF INVENTION

The invention relates to phenol-free, liquid phosphites, based in part on pentaerythritol, which can be used to stabilize organic polymers, especially polyvinyl chloride.

BACKGROUND OF THE INVENTION

Liquid organic phosphites have been used for many years alone and in combination with mixed metal stabilizers for the stabilization of vinyl halide polymers, especially PVC. (Reference: The "Encyclopedia of PVC, Volume 1, L. Nass, Ed., Marcel Dekker Inc., New York, 1977). The phosphite esters employed may be trialkyl, triaryl, mixed alkyl/aryl, and even polymeric.

The problem of imparting polyvinyl chloride with sufficient heat processing stability at temperatures at which the polymer becomes sufficiently fluid or softened to permit shaping is of course of long standing, and has been satisfactorily resolved by the addition to the polymer of various combinations of known heat stabilizers.

At processing temperatures, the PVC resin can degrade, liberating hydrogen chloride, and discolor, become brittle, and stick to the processing equipment. These problems are overcome by combining with the polymer before heat processing or during heat processing one or more of the well established and conventional heat stabilizers, such as, for example, alkyl tin mercaptides or barium/cadmium or barium/zinc or calcium/zinc salt mixed metal stabilizers, aryl, alkyl and mixed aryl/alkyl phosphites, or combinations of the above.

These stabilizers, in preventing the deterioration of the polymers during processing at high temperatures, also permit manufacture of products with increased intrinsic quality because of the enhancement of their resistance to thermal and light degradation during use. In addition, because of the ability of these products to withstand more rigorous conditions, their versatility is increased and new areas of application are thereby opened.

Without going into details or theory, it has been found that mixed alkyl/aryl phosphites such as diphenylisodecyl phosphite and phosphites based on pentaerythritol give the best overall performance in combination with mixed metal stabilizer systems for the stabilization of PVC.

In recent years there has been much concern with exposure to volatiles from the processing of PVC resin, and the exposure to volatiles from articles shaped from stabilized PVC resin exposed to elevated use temperatures. The volatilization of one or more components, or of the decomposition products therefrom, cause the condensation of these volatile components as "fog" on surfaces adjacent to the PVC articles. It has been found that one of the volatiles from the processing of PVC containing certain stabilizers is phenol. The phenol comes from the phosphite used in combination with the mixed metal stabilizer. There is a great need to eliminate or at least minimize the phenol content of phosphite stabilizers and still have a stabilizer which gives good color and processing stability.

One important objection to the contamination of PVC resins with phenol is based on the use of vinyl chloride polymers in food applications, e.g. in the manufacture of food containers. The use of phenol-free stabilizers prevents the transfer of objectionable odors or materials to food.

A preferred phosphite for use with mixed metal stabilizers is diphenyl isodecyl phosphite, but this stabilizer contains about 50% of total phenol. Other phosphite stabilizers based on dialkyl pentaerythritol diphosphites have been known for some time as effective stabilizers for vinyl polymers. Despite wide usage as stabilizers for vinyl chloride polymers, polyolefins, polyurethanes, styrene polymers, and ABS, this type of phosphite has not been entirely satisfactory. The reason for this is the fact that, because of the method of preparation by transesterification from triphenyl phosphite, the dialkyl pentaerythritol diphosphite is contaminated with phenol. In addition, it is advantageous to use mixed metal/phosphite stabilizer combinations as a single liquid component added to the PVC resin during processing. The dialkyl pentaerythritol diphosphites mentioned above are not easily combined with the liquid mixed metal stabilizers, and on standing, a mixture of the liquid mixed metal stabilizer and the dialkyl or diaryl pentaerythritol diphosphite separates into a lighter liquid layer and a more solid layer of heavy sludge. The dialkyl or diary pentaerythritol diphosphite also has a tendency to separate from the PVC matrix on compounding, causing a phenomenon known as plate-out. This lack of package stability and formation of plate-out greatly reduces the usefulness of this type of phosphate.

Pentaerythritol type phosphites and vinyl resins stabilized with such phosphites are disclosed in U.S. Pat. No. 3,281,381 by I. Hechenbleikner and F. C. Lanoue. These pentaerythritol phosphites are prepared by the transesterification of triphenyl phosphite with pentaerythritol to give, depending on the molar ratio of the triphenyl phosphite and pentaerythritol, a variety of possible structures. Tetraphosphites are made by using 4 moles of the tri (aromatic phosphit), such as triphenyl phosphite for each mole of the pentaerythritol. "Spiro" products, which are diphosphites, are made from the reaction of two moles of the triaryl phosphite with one mole of pentaerythritol. Mixed cyclic and non-cyclic esters are made by the reaction of three moles of the starting phosphite with each mole of pentaerythritol. Although the phenol formed in the transesterification reaction used to produce these materials from triphenylphosphite is removed by distillation during the preparation, the products still contain quantities of free phenol, and phenol bound as a phosphite ester may be liberated during compounding or mixing.

Hechenbleikner, in U.S. Pat. No. 3,205,250 suggests the use of dialkylpentaerythritol diphosphites as stabilizers for polyvinyl chloride. Such dialkyl pentaerythritol diphosphites are prepared according to U.S. Pat. No. 4,206,103 by the reaction of two moles of an alkyl alcohol with a diphenyl- or dichloropentaerythritol diphosphite, made by the reaction of two moles of triphenylphosphite or phosphorous trichloride with one mole of pentaerythritol. When diphenyl pentaerythritol diphosphite is the reactant, the spiro isomer comprises about half the combined total of spiro and caged isomers in the product. The spiro and caged isomers have the following structures:

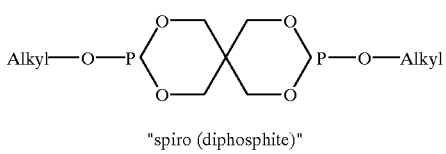

"spiro (diphosphite)"

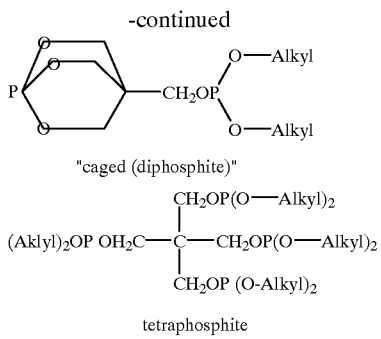

"caged (diphosphite)"

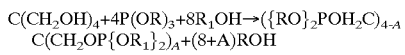

tetraphosphite

When dichloropentaerythritol diphosphite is substituted for the diphenyl pentaerythritol diphosphite, the product which results is the relatively pure spiro isomer, which is generally a solid.

The preparation of dialkylpentaerythritol diphosphites which are not contaminated by the presence of phenol is disclosed in U.S. Pat. No. 4,290,976. The process disclosed utilizes the dichloropentaerythritol diphosphite made from phosphorous trichloride and pentaerythritol as a starting material since it does not contain a phenyl group and there is no possibility of phenol being formed as a contaminant. The products of the process described are characterized by higher set points and as a result do not form stable one-phase mixtures with liquid mixed metal stabilizers.

U.S. Pat. No. 3,047,608 describes the preparation of trialkyl phosphites and dialkyl pentaerythritol diphosphites by transesterification from triphenyl phosphite using a dialkyl or diphenyl phosphite as catalyst. The completeness of the transesterification and the removal of the by-product phenol is controlled by the addition of an excess of the higher aliphatic alcohol, and removal of that excess along with the residual phenol by slow co-distillation under vacuum. The use of the diphenyl phosphites as catalysts, however, is inconvenient and expensive, and the product from reaction of pentaerythritol with two moles of triphenyl phosphite and four moles of the higher aliphatic alcohol is mostly in the spiro form, and is incompatible with liquid mixed metal stabilizers.

Accordingly, there remains a need for essentially phenol free pentaerythritol based phosphites which have good compatibility and package stability with mixed metal stabilizers.

BRIEF SUMMARY OF THE INVENTION

One aspect of the present invention is a phosphite useful as a thermal stabilizer in vinyl polymers, especially polyvinyl chloride resin, of very low or nil phenol content which is compatible with liquid mixed metal stabilizers.

It is another aspect of the present invention to provide a phenol-free octaalkylpentaerythritol tetraphosphite, such as octaisododecylpentaerythritol tetraphosphite.

It is yet another aspect of the present invention to provide a stable single phase mixture of a liquid mixed metal stabilizer and an alkyl pentaerythritol phosphite.

Yet another aspect of the invention is to prepare halogen containing vinyl and vinylidene resin composites showing improved resistance to discoloration and plate-out on exposure to the action of heat and processing. Still another aspect of this invention is to prepare stabilized polymers, especially polyolefins, polyurethanes, styrenic polymers, and ABS using the pentaerythritol tetraphosphites.

A still further aspect of the invention relates to a phosphite derived from pentaerythritol, triphenylphosphite, and alkyl alcohols or alkyl phenols, essentially free of phenol, which has excellent package stability with mixed metal stabilizers and confers superior color and thermal stability to PVC, and is useful in the stabilization of other polymers such as polyolefins, polyurethanes, polystyrenes, and ABS.

In one preferred embodiment of the invention the pentaerythritol phosphite is the reaction product of pentaerythritol, triphenylphosphite (or any phosphite based on a lower alkyl alcohol) and a higher alkyl or mixed alkyl alcohols having carbon chains of at least 8 carbon atoms, with the molar ratio of the reactants being about four moles of the triphenyl phosphite and eight moles of the alkyl alcohol to one mole of pentaerythritol.

DETAILED DESCRIPTION OF THE INVENTION

The alkyl pentaerythritol phosphite of the invention is the reaction product of pentaerythritol, triphenylphosphite and a higher alkyl or mixed alkyl or alkaryl alcohols having a at least 8 carbon atoms, straight-chain or branched, up to about 30 carbon atoms. The reaction product is made by the following reaction scheme:

$$C(CH_2OH)_4 + 4P(OR)_3 + 8R_1OH \rightarrow (\{RO\}_2POH_2C)_{4-A}$$
$$C(CH_2OP\{OR_1\}_2)_A + (8+A)ROH$$

wherein A generally averages from about 3.5 to about 4.0 based upon a plurality of molecules, and preferably is 4. That is, desirably the phosphite compound does not contain the untransesterified "R" group as found in the $P(OR)_3$ compound. R is an aliphatic group, a cycloalkyl or alkyl substituted cycloalkyl, an aryl, an aryl substituted alkyl, or an alkyl substituted aryl of from 1 to about 7 carbon atoms, such as phenyl, methyl, ethyl, propyl, isopropyl, n-butyl, sec-butyl, isobutyl, tert-butyl, $C_5H_{11}$, $C_6H_{13}$, cyclohexyl, $C_7H_{15}$, or cycloheptyl; $R_1$ is an aliphatic group of 8 to 20 carbon atoms, straight chain or branched, cycloalkyl or alkyl substituted cycloalkyl of 8 to 20 carbon atoms, aryl substituted alkyl of 8 to 20 carbon atoms, alkyl substituted aryl of 8 to 20 carbon atoms, or combinations thereof. As apparent from the above formulation, preferred phosphite stabilizers are the tetraphosphites containing pentaerythritol groups therein and the same are compatible with various polymers.

In the invention, the mole ratio of pentaerythritol to starting phosphite to higher aliphatic alcohol can vary over a wide range but generally is from about 1-4-6 to about 1-4-10, desirably from about 1-4-7.8 to about 1-4-8.8, and preferably about 1-4-8 to 1-4-8.5.

Examples of $P(OR)_3$, the starting phosphite, include trimethyl phosphite, triethyl phosphite, tripropyl phosphite, triisopropyl phosphite, tributyl phosphite, tripentyl phosphite, trihexyl phosphite, and triphenyl phosphite. Examples of the alcohols $R_1OH$ include all octyl alcohols, all nonyl alcohols, all decyl alcohols, all dodecyl alcohols, all $C_{12-14}$ mixed alcohols, all $C_{12-16}$ mixed alcohols and blends, and $C_{8-20}$ alkyl or $C_{8-30}$ alkylaryl alcohols, and $C_{8-16}$ alkyl substituted phenols.

The phosphites of the invention can be prepared by the general reaction of the starting phosphite, preferably triphenyl phosphite, with the various alcohols and pentaerythritol, with or without a trace catalyst such as sodium hydroxide. The reaction is heated to a temperature of from about 120° C. to about 170° C. and desirably from about 130° C. to about 150° C. and phenol is distilled off. The reaction is usually completed at a temperature of about 150° C. under a vacuum. The vacuum pulls off the phenol and drives the reaction to completion. Also to remove the residual phenol to the desired (low) level, an excess of the higher aliphatic alcohol is added and the distillation continued, removing the excess along with the residual phenol.

By the term "low residual level" of phenol, it is meant that generally 3% or 2% or less, desirably 1% or 0.75% or less, and preferably 0.5% by weight or less or even nil, phenol remains based upon the weight of the phosphite stabilizer.

When the polymer stabilizer is a halogenated polymer such as PVC, it is very desirable to use liquid mixed metal stabilizers blended with the phosphite stabilizer. A typical liquid stabilizer composition is prepared by mixing an overbased barium nonyl phenate, a liquid zinc carboxylate such as zinc 2-ethylhexanoate, oleic acid, and/or benzoic acid, and a phosphite of this invention. This gives a liquid stabilizer composition containing a mixed metal stabilizer and a phosphite which shows no incompatibility or separation into separate phases on storage.

Mixed metal stabilizers based on typical commercial phenol-free phosphites (such as tridecyl phosphite which contains 6% phosphorous) impart inferior heat stability performance. Mixed metal stabilizers based on typical pentaerythritol diphosphites (such as diisodecyl pentaerythritol diphosphite which contains 0.5 mole of pentaerythritol per mole of phosphorous) are good stabilizers but usually exhibit package instability or phase separation problems. The mixed metal stabilizers which are utilized in this invention are compositions of a neutral zinc carboxylate which is a liquid at ambient temperature, such as zinc octanoate (as opposed to zinc stearate which is a solid), a liquid neutral or overbased barium nonyl phenate (as opposed to a solid barium carboxylate), and small amounts of other additives such as stearic acid or benzoic acid which are soluble in the stabilizer mixture, giving a clear, one-phased mixture.

The amount of the one or more phosphites of the present invention, desirably the noted tetraphosphite when utilized with the halogenated polymers such as polyvinylchloride is generally from about 0.5 to about 5 parts by weight, and desirably from about 1.0 to about 2.5 parts by weight for 100 parts by weight of a halogenated resin. Of course, as noted above, a halogen resin is stabilized, the phosphate is added in a physical blend with the various metal esters or stabilizers noted hereinabove. The phosphite stabilizers of the present invention can also be utilized with other polymers such as polyolefins made from olefin monomers having from 2 or 3 to 6 carbon atoms and thus include polyethylene, polypropylene, polybutadiene, and the like. Other polymers which can be stabilized include the vast number of different types of polyurethanes such as those derived from intermediates containing ethylene oxide, propylene oxide repeat units, i.e. polyesters, or polyester intermediates, which are reacted with various di- or tri-isosyanates including aliphatic, as well as aromatic, and alkyl substituted aromatic di-isosyanates such as methylene di-isosyanate. Another group of polymers include the various styrenic polymers such as polystyrene, poly alpha-methylstyrene, and the like. Still another type of polymer includes the ABS (acrylonitrile-butadiene-styrene) polymers. Other polymers include polyacrylates, polyethers, and the like. The amount of the stabilized phosphites of the present invention with such polymers other than the non-halogenated polymers is from about 0.1 to about 2.5 parts by weight and desirably from about 0.5 to about 1.5 or 2.0 parts by weight for every 100 parts by weight of the polymer.

Stabilized PVC resin compositions are prepared by blending together PVC homopolymer, plasticizer, epoxidized soybean oil, optionally filler and pigment, and the above stabilizer composite of the mixed metal stabilizer and the phosphite of this invention and milling the composition on a 2-roll mill for 5 minutes. The flexible films are sheeted off the mill, cut into strips and tested in a circulating air oven at 200° C. The stabilized PVC composition showed superior resistance to discoloration end an extended time to blackening, indicating superior heat stability of the composition. Stabilized polymers other than PVC are similarly prepared such as by adding the stabilizer to the polymer along with suitable compounding aids such as filler, pigment, and the like and milling the same on a heated roll or otherwise, for a suitable amount of time. Improved properties were once again obtained with regard to resistance to this discoloration and very low amounts of phenol.

We have found that the pentaerythritol phosphite based on 1 mole of pentaerythritol per 4.0 moles of phosphorous, and 8.0 moles plus of isodecyl alcohol gives heat stability performance as good as diphenylisodecyl phosphite which is the industrial standard commonly used phosphite, when used in a mixed metal stabilizer package for PVC. This phosphite is essentially phenol free and gives excellent stabilization, and we found this pentaerythritol phosphite also gives excellent package stability unlike the present commercial pentaerythritol phosphites.

The invention is further described in the following examples, which are included for the purpose of illustration and not for limitation of the scope of the present invention.

EXAMPLES

Example 1.

34.0 g. (0.25 mole) of pentaerythritol, 316.0 g. (2.00 moles) of isodecanol, and 310.0 g. (1.00 mole) of triphenyl phosphite are mixed and heated to 130° C. for 2 hours. After 2 hours, the liberated phenol is stripped off under a slight vacuum. After 2 hours of vacuum stripping, the batch is cooled, yielding 378 g. of clear liquid product as residue in the reaction flask. The distillate was 283 g. (3.0 moles) of phenol containing some isodecyl alcohol.

Example 1 yielded Phosphite 1, i.e. octaisodecylpentaerythritol tetraphosphite.

Example 2.

(comparative example)

158.0g. (1.00 moles) of isodecanol, and 310.0 g. (1.00 moles) of triphenyl phosphite are mixed and heated to 130° C. for 2 hours. After 2 hours the liberated phenol is stripped off under a slight vacuum. After 2 hours of vacuum stripping the batch is cooled. The clear liquid product (374 g.) is obtained as a residue in the reaction flask. The phenol (94 g.) is recovered as the distillate. This phosphite is known as diphenyl isodecyl phosphite.

Example 2 yielded Phosphite 2, i.e. diphenylisodecyl phosphite.

Example 3.

34.0 g. (0.25 mole) of pentaerythritol. 200.0 g. (1.00 moles) of tridecanol, 220.0 g. (1.00 moles) of nonylphenol, and 310.0 (1.00 moles) of triphenyl phosphite are mixed and heated to 130° C. for 2 hours. After 2 hours, the liberated phenol is stripped off under slight vacuum. After 2 hours of stripping, the batch is cooled. The clear liquid product, (374 g.) is obtained in the reaction flask. Phenol (28'3 g.) is recovered in the distillation receiver.

Example 3 yielded Phosphite 3, i.e. a mixture with the average composition of tetratridecyl and tetranonylphenyl pentaerythritol tetraphosphite.

The properties of the above cited phosphites are as follows:

| Material | % P | CPS/25° C. | Color, APHA | Acid # | % Total Phenol |
|---|---|---|---|---|---|
| Ex. 1-Phosphite 1 | 8.1 | 24 | 30 | 0.1 | 1.2 |
| Ex. 2-Phosphite 2 (Control) | 8.3 | 14 | 50 | 0.1 | 50.0 |
| Ex. 3-Phosphite 3 | 5.4 | 55 | 20 | 0.1 | Nil |
| Control-Phosphite 4 (Trilsodecyl phosphite) | 6.2 | 15 | <50 | 0.1 | 2.0 |

As apparent from the above data, the stabilized phosphites of the present invention containing pentaerythritol, i.e. Examples 1 and 3 gave very low contents of phenol as in comparison with a Control, i.e. Example 2 which contain diphenyl isodecyl phosphite.

Examples of commercial phosphites that are currently used with mixed metal stabilizers are as follows: (comparative examples)

| Phosphite Material | % P | CPS/25° C. | Color, APHA | Acid # | % Total Phenol |
|---|---|---|---|---|---|
| phenyldiisodecyl | 7.1 | 17 | <50 | 0.05 | 21 |
| diphenylisodecyl (Phosphite 2)* | 8.3 | 14 | <50 | 0.05 | ~50 |
| diphenyloctyl | 9.0 | 9 | <50 | 0.05 | ~54 |
| triisodecyl (Phosphite 5) | 6.2 | 15 | <50 | 0.1 | ~20 |
| tris(tridecyl) | 4.9 | 41 | <50 | 0.1 | ~2.0 |
| trilauryl | 5.3 | 20 | <50 | 0.1 | ~2.0 |

*This commercial phosphite, diphenylisodecyl, is also phosphite 2 cited in this study, and is used as the standard for comparison of the stabilization performance.

Example 5.

(Testing Example)

Each of the above phosphites (Examples 1 through 4) were evaluated in a flexible PVC resin using the following formulation:

| | |
|---|---|
| PVC | 100 parts |
| Dioctyl phthalate | 38 parts |
| ESO | 2 parts |
| Stearic Acid | 0.2 parts |
| Phosphite (1–5) | 1 part |
| Mixed Metal Stabilizer* | 2 parts |

*The mixed metal stabilizer is a 1:1 combination of Barium nonyl phenate (12% Ba) and Zinc 2-ethylhexanoate (12% Zn) (with additional minor components) known as Barostab B-148 from Barlocher USA.

The formulations were blended and milled on a two-roll mill 0.03" thick at 180° C. for 5 minutes. The films were cut into ½" strips and tested in a circulating air oven at 195° C. (Werner-Mathis Thermotester). The color of the samples was observed continuously as the strips were withdrawn from the heated zone of the oven and time to discoloration or black was noted.

Testing Results:

| Phosphite | % P | % Phenol (1) | Time, minutes (2) |
|---|---|---|---|
| Phosphite 1 | 8.1 | Nil | 22.0 |
| Phosphite 2 | 8.2 | 0.2 | 21.5 |
| Phosphite 3 | 6.4 | Nil | 20.5 |
| Phosphite 4 | 6.2 | Nil | 19.0 |

(1) % phenol in total PVC formulation.
(2) Minutes elapsed before discoloration.

Compared to Phosphite 2 or isodecyl diphenyl phosphite which is not phenol-free, but currently used widely in the PVC industry, Phosphite 1 of this invention is not only essentially phenol-free but also is an excellent heat and color stabilizer for PVC and has excellent package stability with liquid mixed metal stabilizers.

While in accordance with the patent statutes the best mode and preferred embodiment have been set forth, the scope of the invention is not limited thereto but rather by the scope of the claims.

What is claimed is:

1. A pentaerythritol phosphite having the formula:

wherein A is from about 3.5 to about 4.0 based upon a plurality of molecules, wherein R is hydrocarbon having from 1 to about 7 carbon atoms, and wherein each $R_1$, independently, is an aliphatic group of 8 to 20 carbon atoms, straight chain or branched; or a cycloalkyl or alkyl substituted cycloalkyl of 8 to 20 carbon atoms, or an aryl substituted alkyl of 8 to 20 carbon atoms, or an alkyl substituted aryl of 8 to 20 carbon atoms, or combinations thereof, and wherein at least one said $R_1$, independently, is said aliphatic having from 8 to 20 carbon atoms, or said cycloalkyl or alkyl substituted cycloalkyl having from 8 to 20 carbon atoms.

2. A phosphite as claimed in claim 1, wherein $R_1$ is an isodecyl group.

3. A phosphite as claimed in claim 1, wherein R is an aliphatic straight chain or branched, cycloalkyl or alkyl substituted cycloalkyl, aryl, aryl substituted alkyl, or alkyl substituted aryl and wherein each said $R_1$, independently, is an aliphatic group of 8 to 20 carbon atoms, straight chain or branched, or a cycloalkyl or alkyl substituted cycloalkyl of 8 to 20 carbon atoms.

4. A phosphite as claimed in claim 3, wherein R is phenyl, methyl, ethyl, propyl, isopropyl, n-butyl, sec-butyl, isobutyl, tert-butyl, $C_5H_{11}$, $C_6H_{13}$, cyclohexyl, $C_7H_{15}$, or cycloheptyl.

5. A phosphite as claimed in claim 4, including less than about 3% by weight of phenol as an impurity based upon the weight of said phosphite.

6. A phosphite according to claim 5, wherein A is about 4, wherein $R_1$ is a dodecyl group or an octyl group, and wherein the amount of phenol as an impurity is about 1% or less by weight based upon the weight of said phosphite.

7. A phosphite as claimed in claim 1, wherein said phosphite is a tetraphosphite.

8. A phosphite as claimed in claim 1, comprising an octaisodecylpentaerythritol tetraphosphite or octadodecylpentaerythritol tetraphosphite, or octadecylpentaerythritol tetraphosphite.

9. A method for stabilizing a polymeric resin, comprising the steps of:

mixing the resin with at least one pentaerythritol phosphite having the formula

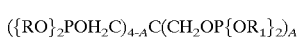

wherein A is from about 3.5 to about 4.0 based upon a plurality of molecules, wherein R is a hydrocarbon having from 1 to about 7 carbon atoms, and wherein each $R_1$, independently, is an aliphatic group of 8 to 20 carbon atoms, straight chain or branched; or a cycloalkyl or alkyl substituted cycloalkyl of 8 to 20 carbon atoms, or an aryl substituted alkyl of 8 to 20 carbon atoms, or an alkyl substituted aryl of 8 to 20 carbon atoms, or combinations thereof, and wherein at least one said $R_1$, independently, is said aliphatic having from 8 to 20 carbon atoms, or said cycloalkyl or alkyl substituted cycloalkyl having from 8 to 20 carbon atoms.

10. A method according to claim 9, wherein R is an aliphatic straight chain or branched, cycloalkyl or alkyl substituted cycloalkyl, aryl, aryl substituted alkyl, or an alkyl substituted aryl and wherein each said $R_1$, independently, is an aliphatic group of 8 to 20 carbon atoms, straight chain or branched, or a cycloalkyl or alkyl substituted cycloalkyl of 8 to 20 carbon atoms.

11. A method according to claim 9, wherein said phosphite is a tetraphosphite, and wherein R is phenyl, methyl, ethyl, propyl, isopropyl, n-butyl, sec-butyl, isobutyl, tert-butyl, $C_5H_{11}$, $C_6H_{13}$, cyclohexyl, $C_7H_{15}$, or cycloheptyl.

12. A method according to claim 10, wherein said polymeric resin is polyvinyl chloride, and including mixing said resin with a mixed metal stabilizer.

13. A method according to claim 12, wherein said mixed metal stabilizer comprises a mixture of an overbased barium nonyl phenate and a liquid zinc carboxylate, and wherein said pentaerythritol phosphite is octylisodecylpentaerythritol tetraphosphite, or octadodecylpentraerythritol tetraphosphite, or octadecylpentraerythritol tetraphosphite.

14. A method according to claim 13, wherein the amount of said pentaerythritol phosphite is from about 0.5 to about 5 parts by weight per 100 parts by weight of said resin.

15. A method according to claim 11, wherein said resin is a polyolefin, a polyurethane, a styrenic polymer, an ABS copolymer, a polyacrylate, or a polyether, or combinations thereof, and wherein the amount of said pentaerythritol phosphite is from about 0.1 to about 2.5 parts per 100 parts by weight of said polymer.

16. A method according to claim 15, wherein said pentaerythritol phosphite is octaisodecylpentaerythritol tetraphosphite or octadodecylpentraerythritol tetraphosphite, or octadecylpentraerythritol tetraphosphite.

17. A stabilized polymer comprising:
a polymeric resin, and
a liquid stabilizer comprising:
a) at least one pentaerythritol phosphite having the formula:

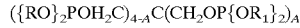

$(\{RO\}_2POH_2C)_{4-A}C(CH_2OP\{OR_1\}_2)_A$ wherein A is from about 3.5 to about 4.0 based upon a plurality of molecules, wherein R is hydrocarbon having from 1 to about 7 carbon atoms, and wherein each $R_1$, independently, is an aliphatic group of 8 to 20 carbon atoms, straight chain or branched; or a cycloalkyl or alkyl substituted cycloalkyl of 8 to 20 carbon atoms, or an aryl substituted alkyl of 8 to 20 carbon atoms, or an alkyl substituted aryl of 8 to 20 carbon atoms, or combinations thereof, and wherein at least one $R_1$, independently, is said aliphatic having from 8 to 20 carbon atoms, or said cycloalkyl or alkyl substituted cycloalkyl having from 8 to 20 carbon atoms and b) optionally at least one mixed metal stabilizer.

18. A stabilized polymer according to claim 17, wherein R is phenyl, methyl, ethyl, propyl, isopropyl, n-butyl, sec-butyl, isobutyl, tert-butyl, $C_5H_{11}$, $C_6H_{13}$, cyclohexyl, $C_7H_{15}$, and cycloheptyl, and wherein each said $R_1$, independently, is an aliphatic group of 8 to 20 carbon atoms, straight chain or branched, or a cycloalkyl or alkyl substituted cycloalkyl of 8 to 20 carbon atoms.

19. A stabilized polymer according to claim 18, wherein said resin is polyvinyl chloride, and including said mixed metal stabilizer.

20. A stabilized polymer according to claim 19, wherein the amount of said stabilizer is from about 0.5 to about 5 parts by weight per 100 parts by weight of said polyvinyl chloride, wherein A is about 4.0, and wherein the amount of mixed metal stabilizer is from about 0.5 parts to about 5.0 parts by weight per 100 parts by weight of said polymer.

21. A stabilized polymer according to claim 19, wherein said alkyl pentaerythritol phosphite is octylisodecylpentaerythritol tetraphosphite, or octadodecylpentraerythritol tetraphosphite, or octadecylpentraerythritol tetraphosphite.

22. A stabilizer according to claim 20, wherein said phosphite is a tetraphosphite.

23. A stabilized polymer according to claim 18, wherein said polymer is a polyolefin, a polyurethane, a styrenic polymer, an ABS copolymer, a polyacrylate, or a polyether, or combinations thereof.

24. A stabilized polymer according to claim 23, wherein the amount of stabile phosphite stabilizer is from about 0.1 to about 2.5 parts by weight per 100 parts by weight of said polymer.

25. A stabilized polymer according to claim 24, wherein said alkyl pentaerythritol phosphite is octylisodecylpentaerythritol tetraphosphite or octadodecylpentraerythritol tetraphosphite, or octadecylpentraerythritol tetraphosphite.

* * * * *